United States Patent [19]

Bentley

[11] 3,935,111

[45] Jan. 27, 1976

[54] DEVICE FOR REMOVING BLOOD MICROEMBOLI

[75] Inventor: Donald J. Bentley, Newport Beach, Calif.

[73] Assignee: Bentley Laboratories, Inc., Irvine, Calif.

[22] Filed: Apr. 6, 1973

[21] Appl. No.: 348,588

[52] U.S. Cl. .......... 210/446; 210/489; 210/DIG. 23
[51] Int. Cl.² ........................................ B10D 25/00
[58] Field of Search............... 55/487, 488, DIG. 13; 210/335–336, 418, 445–456, 210/489, DIG. 23, 500

[56] References Cited
UNITED STATES PATENTS

| | | | |
|---|---|---|---|
| 2,696,818 | 12/1954 | Van Loghem | 210/DIG. 23 |
| 3,276,597 | 10/1966 | Mesek et al. | 210/489 |
| 3,448,041 | 6/1969 | Swank | 210/446 X |
| 3,593,854 | 7/1971 | Swank | 210/446 X |
| 3,682,386 | 8/1972 | Herman | 210/418 X |
| 3,747,769 | 7/1973 | Brumfield | 210/DIG. 23 |
| 3,765,536 | 10/1973 | Rosenberg | 210/DIG. 23 |

*Primary Examiner*—Charles N. Hart
*Assistant Examiner*—Richard W. Burks
*Attorney, Agent, or Firm*—Lyon & Lyon

[57] ABSTRACT

A device for removing microemboli including microparticles and aggregates of various types including degenerated blood elements from whole blood or other transfusible materials, such as packed red cells and other blood components. The device has a casing with an interior chamber and is provided with externally-connectable flow inlet and flow outlet ports relative to the interior of the chamber, with a plurality of effective layers of microemboli-removing material positioned in the chamber and sealed to the inner periphery of the casing to require blood flow therethrough in travel of the blood from the flow inlet to the flow outlet. Each of said layers of microemboli-removing material consists of a foamed open cell polyurethane to define tortuous flow passages therethrough and with the layers having progressively smaller effective pore sizes whereby the blood in flowing therethrough has substantially all of the microemboli of a size to block passages in a layer prevented from flowing thereto by adherence to the walls of the tortuous passages in a preceding layer of said material. Two different embodiments are shown, with one embodiment having bypass structure.

16 Claims, 6 Drawing Figures

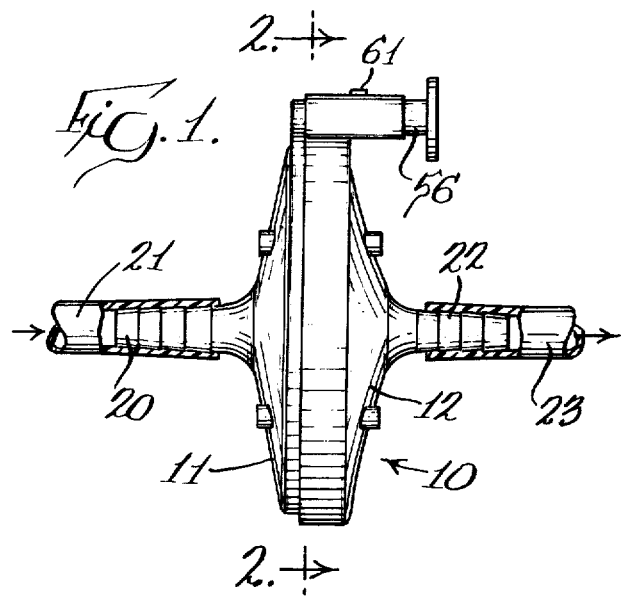
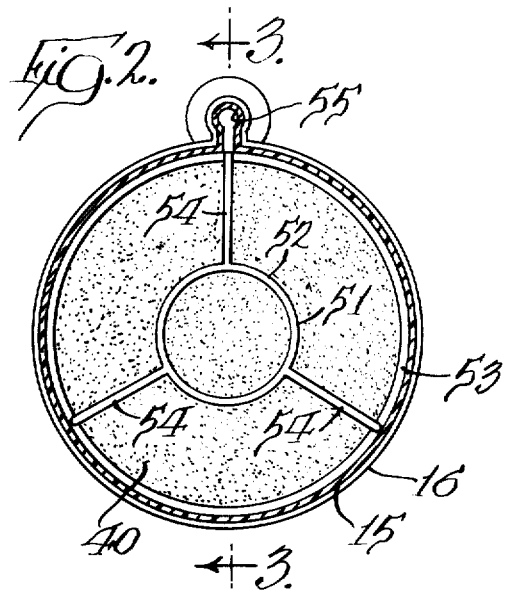
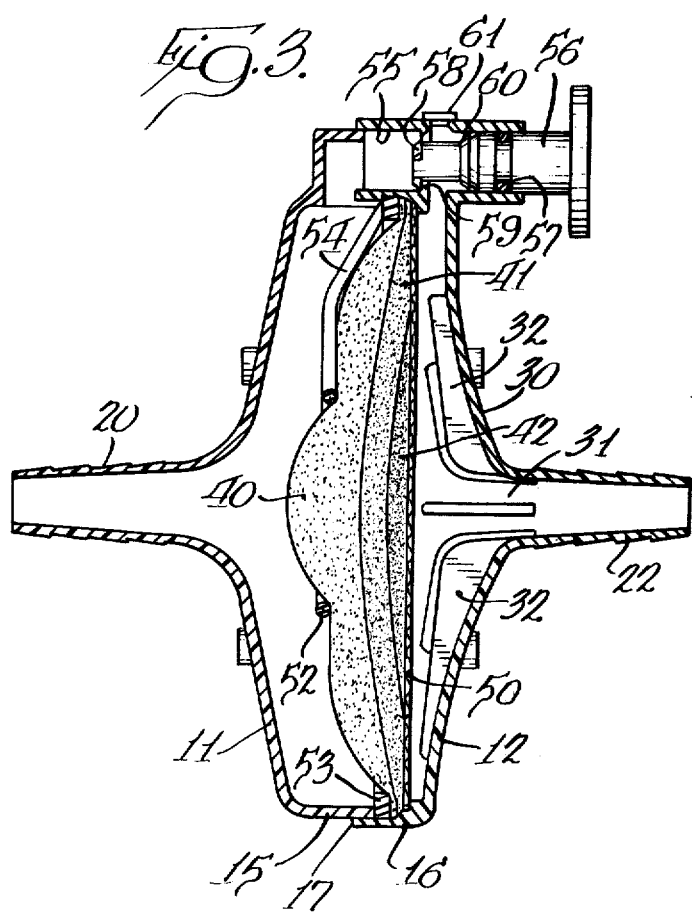
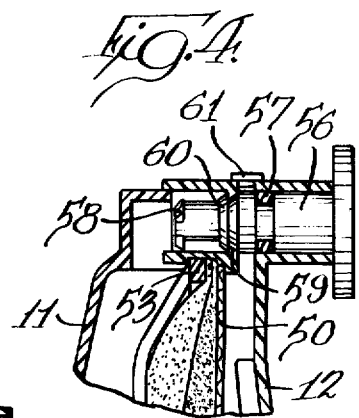

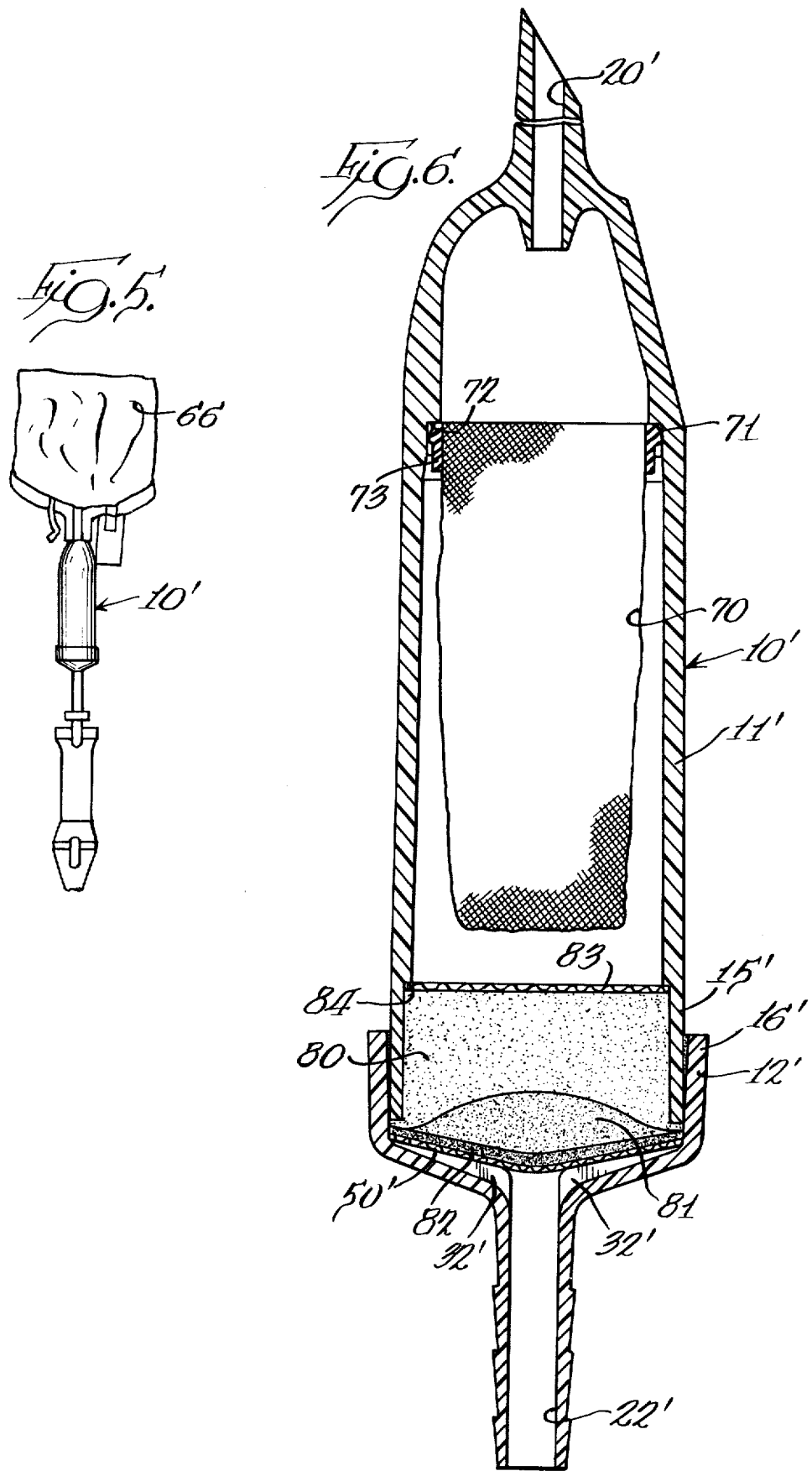

DEVICE FOR REMOVING BLOOD MICROEMBOLI

BACKGROUND OF THE INVENTION

This invention pertains to medical devices for removing various types of microemboli from whole blood or the like and from both venous and arterial blood in extracorporeal circulation systems as well as in infusion of blood bank blood to a patient.

DESCRIPTION OF THE PRIOR ART

In recent years, investigators have found that blood bank-blood rapidly deteriorates in storage after the first few days with the formation of aggregates of blood components, such as altered platelets and leukocytes which become adhesive. Platelets range upwardly in size from 2 microns, with red cells being somewhat larger and white cells being approximately 20 microns. In addition to the foregoing microemboli, there are also other agglomerates, such as fat agglomerates. Investigators have referred to a "buffy coat" which is that layer of material in a centrifuge sample of whole blood between the red cells and the plasma and which contains sticky platelets, fat agglomerates and broken red cell debris. These various agglomerates and aggregates have been found to be of varying sizes, with the size thereof in many instances being less than 5 microns, but in some cases being up to a size of 100 microns in longest diameter. Thus in many instances, the microemboli are of a size smaller than usable parts of the blood including the red cells and a good share of the components in the plasma.

Problems with microemboli are also known in extracorporeal circulation systems with damaged blood components being circulated.

In both instances, namely, infusion of whole blood or the like as well as in extracorporeal circulation systems, the microemboli should be removed before delivery to the patient, since the microemboli may cause adverse effects on the patient. For example, the microemboli have been found to collect in the capillaries and cause occlusion of the capillaries.

Many different types of filter media have been investigated and certain filter media have been in actual use.

One form of filter media utilizes a compacted layer of glass fiber wool or a wool formed from other materials, such as DACRON.

The filter media functions to catch the microemboli on the fibers thereof, with this action aided by the adhesive nature of the microemboli, and thus strains the micreoemboli from the blood flow. This tends to build up a blocking layer to blood flow and an increase of the pressure of the blood to obtain flow through the filter may result in additional damage to the blood.

The filter media does not provide for specific control of the size of the flow passages and, therefore, there can be a channeling effect with the blood taking the easiest flow path. This does not provide a positive control to assure that the blood leaving the filter assuredly has no potentially damaging microemboli. Any attempt to have the passages of a size less than the size of a microemboli would not be satisfactory because the resulting size would result in straining from the blood the desirable components thereof which may be of a lesser size than the microemboli.

SUMMARY

The invention disclosed herein has, as a primary concept, the use of a microemboli removal element having a multiplicity of elongated passageways extending through the thickness direction of the removal element, with each passageway being largest on the inflow side and progressively decreasing in diameter along the passageway length, so that at the outflow side the passageways are generally of smallest cross section. The damaged particles of blood tend to have an adhesiveness and, from a statistical standpoint, the larger portions of the passageways on the inflow side of the removal element are more apt to come into adherence with the largest damaged blood particles. Similarly, the intermediate sized damaged blood particles are most apt to adhere to the side walls of the intermediate sized portions of the passageways, thus leaving the smaller damaged particles for adherence to the side walls of the smaller portions of the passageways near the outflow side of the removal element. Some small and intermediate size damaged blood particles may adhere near the inflow side of the removal element to the passageways. However, for the most part, there is a selective progressive removal of biologically damaged blood particles which are subjected to flow for a period of time through a removal element of substantial thickness.

The flow passageways are of a length to provide the damaged blood particles with a substantial opportunity to engage and adhere to a wall and, thus, the wall surfaces of all the passageways are potentially effective to remove undesired blood particles. As part of the primary concept, the removal element builds up a collection of damaged blood particles on the walls of the passageways, rather than at the inflow surface of the removal element to avoid clogging of blood flow through the removal element, whereby there can be a continuous flow of undamaged blood. The damaged blood particles are effectively collected on the walls of the passageways of the removal element by adsorption by exposing the damaged blood particles over a period of time to the passageways of the removal element. This enables the utilization of the entire thickness of the removal element in removing damaged particles of blood, some of which may be smaller in size than undamaged usable portions of the blood.

Blood flows through the removal material having tortuous passages with an initial effective pore size greater than that of the size of the microemboli with adherence of said microemboli to the walls of said passages during flow therethrough with progressively decreasing effective pore sizes throughout the removal structure whereby microemboli of a size larger than the effective pore size at a certain level of the removal structure will have been removed upstream thereof to avoid any mechanical straining or filtering of the microemboli from the blood which would tend to clog the entry to any portion of the tortuous flow passages of the microemboli-removing material.

Another primary feature of the inventive concept is the provision for the microemboli removal by use of the principles set forth in the preceding paragraphs wherein the microemboli-removing material is formed from a foamed open cell polyurethane and with the material having several effective layers, with the first layer encountered by the blood flow therethrough having an effective pore size greater than the size of the microemboli to be removed and with the effective pore size going through a series of stepped reductions in the effective layers of the material and with the final effective layer having a much smaller effective pore size whereby the blood leaving the device will have harmful microemboli removed therefrom.

The invention utilizes open cell foamed plastic having a plurality of effective layers with tortuous passages therethrough and with the effective pore size of the initial effective layer being greater than the size of the microemboli to be removed from the blood and with a progressive reduction in the effective pore size through the effective layers whereby a build-up of microemboli does not occur on the surface of the material to block blood flow therethrough nor is there a build-up at the entry level of any of the succeeding effective layers because of the adherence of the larger microemboli in a preceding effective layer of the material. This avoids mechanical obstruction or straining of the microemboli from the blood with a resultant potential for build-up of a blood flow blocking layer on the surface of a mechanical-type filter with resultant malfunctioning in the infusion or extracorporeal circulation system.

An object of the invention is to provide a device for removing microemboli from whole blood or the like wherein the blood flow is caused to travel through a plurality of effective layers of microemboli-removing material of an open cell foamed plastic with the effective layers defining tortuous flow passages therethrough and with the effective layers having progressively smaller effective pore sizes whereby the blood in flowing therethrough has the microemboli of a size to block passages in a layer prevented from flowing thereto by adherence to the walls of the passages in a preceding layer and wherein the initial effective layer has an effective pore size larger than the largest diameter of substantially all of the microemboli.

Another object of the invention is to provide a device for removing microemboli from whole blood or the like as described above and having the inventive concepts wherein the plurality of effective layers of microemboli-removing material are of an open cell foamed polyurethane with such material having been tested and found to not be harmful to blood.

An additional object of the invention is to provide a microemboli-removing device wherein the effective layers of microemboli-removing material are mounted within an interior chamber of a casing having a housing member and a base member and provided with a flow inlet to the chamber and a flow outlet therefrom and with the housing member and base member telescopically interfitted and capturing the effective layers of removal material therebetween. Said casing may be suitably constructed for use in a blood infusion system or for use in extracorporeal circulation systems and, in the latter instance, may be provided with suitable connections to tubing or may be part of a cardiotomy reservoir. Also, the casing may have provision for bypass of priming fluid.

BRIEF DESCRIPTION OF THE DRAWING

FIG. 1 is a vertical elevation of a first embodiment of the microemboli-removing device for use in extracorporeal circulation systems;

FIG. 2 is a vertical section, taken generally along the line 2—2 in FIG. 1;

FIG. 3 is a vertical section of the device and taken generally along the line 3—3 in FIG. 2;

FIG. 4 is a framentary view of a part of the structure shown in FIG. 3 and in a locked position;

FIG. 5 is a vertical elevation of a second embodiment of the microemboli-removing device for use in the infusion of blood; and FIG. 6 is a central vertical section through said second embodiment of the microemboli-removing device.

DESCRIPTION OF THE PREFERRED EMBODIMENTS

The first embodiment of the invention is shown in FIGS. 1–4 and is a preferred form for use in extracorporeal circulation systems and particularly where the device is connected into a tubular path for the blood. The device embodies a casing, indicated generally at 10, made up of a housing member 11 and a base member 12 which are generally circular in cross-section and which have a major diameter section defined by a peripheral wall 15 for the housing member and a peripheral wall 16 for the base member 12. These two parts are assembled by telescopic interfitting of the walls, one within the other, and a suitable bonding of the parts together. A suitable material for forming the housing member and base member is polycarbonate and a solvent may be applied to obtain the bonding of the two members together with the solvent being applied at 17.

The casing 10 has an interior chamber with a flow inlet 20 defined by a reduced diameter tubular portion of the housing member 10 and which has shapes on its outer surface for insertion and locking into a tube 21.

A flow outlet 22 is defined by a reduced diameter tubular part of the base member 12 and having suitable shaping on the exterior thereof for locking into a tube 23.

The housing member 10 has a generally uniform wall thickness with the peripheral wall 15 being of an outer diameter slightly less than the inner diameter of peripheral wall 16 of the base member 12 whereby the first-mentioned wall may fit into the interior of the last-mentioned wall to define the interior chamber. The base member 12 has a radially extending wall 30 with a series of channels 31 spaced apart by integral ribs 32 and which slope toward the flow outlet 22.

The microemboli-removing material is shown as formed of discrete layers 40, 41 and 42. These layers are supported in position within the casing by a support member 50 in the form of screen material having relatively large openings spanning the interior chamber of the casing and assuring blood flow paths in the channels 31 of the base member 12 by the support of the microemboli-removing material.

The three discrete layers 40–42 vary in thickness in the embodiment shown with layer 40 being of the greatest thickness, layer 41 of a medium thickness, and the final layer 42 being the thinnest. The final layer 42 is of the same diameter as the other layers, but does not show completely in FIG. 3 because of its compression.

The effective layers 40–42 are formed of an open cell foamed plastic and, more particularly polyruethane, and with the diameter of the layers 40–42 being the same as the diameter of the base member 12 within the peripheral wall 16. The layers of material 40–42 are held against the support member 50 by a retainer 51 having inner and outer rings 52 and 53 and interconnecting ribs 54. The assembly of the layers within the base member 12 followed by insertion of the housing member 11 against retainer ring 53 results in compression of the periphery of these layers, as shown in FIG. 3, with a securing of these layers in position by the peripheral wall 15 of the housing member.

The polyurethane is sufficiently flexible to take the shape shown in FIG. 3, although the layers were initially flat.

As stated previously, microemboli to be removed from the whole blood or the like, such as, packed red cells and blood components and aggregates are in most instances less than 50 microns at their largest dimension but some have been found to be greater than 100 microns in diameter. Accordingly, the first layer 40 has tortuous passages therethrough with an effective pore size (being substantially the minimum throat diameter of such passages) of approximately 150 microns. As blood with various aggregates and agglomerates flows through the first layer 40, the effective pore sizes are sufficiently large as to avoid any mechanical straining or filtering at the exposed surface of the first layer 40. The larger aggregates and agglomerates being quite adhesive tend to adhere to the walls of the tortuous passages whereby the blood with aggregates and agglomerates of only a reduced size reaches the second effective layer 41. As an example only, and not to be construed as limiting, the effective pore size of the second effective layer 41 can be 75 microns, with an action similar to that of the first layer 40 occurring where additional aggregates and agglomerates adhesively adhere to the walls of the tortuous passages prior to the blood reaching the third effective layer 42. As an example, the third layer 42 can have effective pore sizes of approximately 30 microns, with similar adhesive adherence of even smaller microemboli. The blood then flows from the flow outlet 22 with the microemboli which should not reach the patient removed by adhesive adherence to the walls of the tortuous passages of the various layers 40–42, while not preventing the flow-through of the usable components of the blood. This action has occurred without any obstructing build-up of such aggregates and agglomerates on the surface of the initial layer 40 or of any of the succeeding effective layers of the microemboli-removing material.

When used in an arterial line, the device should be primed, with flow of a suitable fluid therethrough. This is accomplished by flow of such fluid through the layers 40–42 of material and also by flow through a bypass passage 55 which is a tubular passage formed in the base member 12 and connecting the interior chamber at either side of the layers of material 40–42.

As shown in FIG. 3, a flow-blocking plunger 56 is shown in inactive position whereby there is relatively free flow through the bypass passage 55. After priming, the plunger 56 can be moved to the flow-blocking position shown in FIG. 4 which closes the bypass passage 55. The plunger 56 is generally cylindrical, with a sealing O-ring 57 and with a circumferentially-spaced series of protrusions 58 which limit the outermost position of the plunger 56 as shown in FIG. 3 by one of the protrusions engaging a protrusion 59 formed on the base member 12. Once the bypass operation has been completed and the plunger 56 is moved to the locked position shown in FIG. 4, a flange 60 on the plunger moves behind the projections 59 to hold the plunger in locked position. A removable plug 61 closes an opening in the base member 12 through which air bubbles may be removed from the device.

The general structure as shown in FIGS. 1 and 2 with suitable modifications as to shape may be used in a cardiotomy reservoir.

The second embodiment shown in FIGS. 5 and 6 is of the same basic construction as that of the first embodiment and similar parts have been given the same reference numeral, with a prime affixed thereto. The housing member 11' has a peripheral wall 15' fitted within a peripheral wall 16' of a base member 12' to define a casing 10' with an interior chamber. A reduced, generally tubular part of the housing member 11' is constructed differently from the similar structure in the first embodiment in that it is formed as a sharpened spike for insertion into the outlet of a blood container 66 to enable use of this device in a blood infusion system with the blood flowing to the interior chamber through a flow inlet 20'.

A gross filter 70 in the form of a sock of screen material with a lower closed end and having realtively large openings such as approximately 200 microns is positioned within the chamber with the upper peripheral edge 71 thereof held against an annular flange 72 on the interior of the housing member by a retaining ring 73. This filter collects and retains any clots of a major size that might come into the device from blood bankblood. The whole blood or the like flowing past the gross filter 70 reaches the plurality of effective layers of microemboli-removing material which, in the embodiment of FIGS. 1–4, consists of three effective layers. These layers are of open cell foamed polyurethane as in the embodiment of FIGS. 1 and 2 whereby the same principles of adhesive adherence of microemboli for removal thereof from the flow of whole blood or the like is utilized. As an example, the first layer 80 may have effective pore sizes of approximately 150 microns with the second layer 81 having effective pore sizes of 75 microns and the third layer 82 having effective pore sizes of approximately 30 microns.

An upper screen 83 is fitted against a flange 84 to hold the layers 80–82 in position.

With the device of FIGS. 5 and 6, whole blood or the like flows from the flow outlet 22' with harmful microemboli removed therefrom to avoid harmful effects to a patient, such as occlusion of the capillaries.

An example of a suitable material is polyester urethane. Normally open celled foamed polyurethane is produced with effective pore sizes exceeding 150 microns. In order to enable use of such polyurethane, the open cell foamed polyurethane may be modified to obtain the selected effective pore sizes by obtaining uniform heating throughout the entire thickness of the foamed polyurethane and then compressing the polyurethane to the desired density without sufficient heat being applied to the exterior thereof to raise the temperature of the polyurethane to form a hard dense surface. The compression and resulting density may be selected in order to provide the desired effective pore sizes for the various layers of the microemboli-removing material.

It is within the scope of the invention to form the plural layer microemboli removing material as a unitary structure treated by heat and pressure appropriately so that the passages therethrough are of progressively decreasing cross section.

The polyurethane has approximately the same static electric charge as do undamaged red blood cells, thus the latter exhibit little or no tendency toward adherence to the side walls defining the tortuous flow passages.

With the structures disclosed herein, microemboli may be removed satisfactorily in extracorporeal systems as well as in blood infusion systems and, in the latter instance, enable the use of blood bank-blood which has been in storage for a greater length of time than is now feasible.

I claim:

1. A device for removing microemboli from whole blood or the like comprising: a casing with an interior chamber and with a flow inlet to and a flow outlet from the chamber; a plurality of effective layers of microemboli-removing material positioned in said chamber and sealed to the inner periphery of the casing to require blood flow therethrough in travel of the blood from the flow inlet to the flow outlet, said effective layers each consisting of foamed open cell polyurethane to define tortuous flow passages therethrough, said effective layers having progressively smaller effective pore sizes whereby the blood in flowing therethrough has the microemboli of a size to block passages in a layer prevented from flowing thereto by adherence to the walls of the passages in a preceding layer.

2. A device for removing microemboli from whole blood or the like as defined in claim 1 wherein the initial layer of material has an effective pore size greater than substantially all of the microemboli.

3. A device for removing microemboli from whole blood or the like comprising: a casing with an interior chamber and with a flow inlet to and a flow outlet from the chamber; a plurality of layers of microemboli-removing material positioned in said chamber and sealed to the inner periphery of the casing to require blood flow therethrough in travel of the blood from the flow inlet to the flow outlet, said layers each having a plurality of tortuous passages therethrough with the effective pore size of each layer differing from the other and gradually decreasing in size from the layer closest to the flow inlet; and each of said layers of microemboli-removing material being formed of an open cell foamed plastic.

4. A device for removing microemboli from whole blood or the like as defined in claim 3 and wherein said open cell foamed plastic is polyurethane.

5. A device for removing microemboli from whole blood or the like as defined in claim 4 wherein the effective pore size of the layer of material closest to the flow inlet is larger than substantially all of the microemboli to be removed whereby said microemboli are not mechanically strained from the blood flow at the surface of said last-mentioned layer but may travel into the tortuous passages thereof and adhere to the wall of said passages.

6. A device for removing microemboli from whole blood or the like as defined in claim 5 wherein said casing includes a housing member and a base member with said members being telescopically interfitted to define said interior chamber; and said layers of material being held in position by having their peripheries mechanically captured by said members.

7. A device for removing microemboli from whole blood or the like as defined in claim 6 wherein the device is usable in blood infusion and said housing member has the flow inlet in an end thereof and said end is formed as a spike for insertion into the outlet of a blood container; and a gross filter in said interior chamber ahead of said material layers for collecting large blood clots.

8. A device for removing microemboli from whole blood or the like as defined in claim 7 wherein said gross filter is in the form of a sock; a peripheral flange on the interior of the housing member, and a retainer ring holding the top edge of said sock against said flange.

9. A device for removing microemboli from whole blood or the like as defined in claim 6 wherein said housing member and base member each has adjacent ends with a peripheral cylindrical wall and with the wall of the housing member of a smaller diameter and fitted into the wall of the base member to form said telescopic interfit; and said base member having a support of screen material underlying said layers of material and spanning the flow outlet to support said layers.

10. A device for removing microemboli from blood as defined in claim 8 including blood flow channels in the base member adjacent said screen material support to facilitate blood flow to the flow outlet.

11. A device for removing microemboli from whole blood or the like as defined in claim 9 with a bypass passage around said layers of material, and a plunger movable to a position to close said passage.

12. A device for removing microemboli from whole blood or the like comprising: a casing defined by a housing member and a base member received together to define an interior chamber; an externally connectable flow inlet to the chamber in one member; an externally connectable flow outlet from the chamber in the other member; a plurality of layers of microemboli-removing material positioned in said chamber in obstructing relation to the flow path from the flow inlet to the flow outlet, said layers each consisting of foamed open cell polyurethane to define tortuous flow passages therethrough, the first layer closest to the flow inlet having an effective pore size for the passages greater than the size of substantially all microemboli to be removed from the blood whereby the microemboli may enter the passages and the largest thereof adhesively adhere to the wall thereof to prevent further flow of the largest microemboli, the successive layers of material having progressively smaller effective pore size to receive progressively smaller microemboli and cause adherence thereof to the passage walls, said smaller effective pore sizes being less than the size of microemboli retained by the previous layer of material but not being blocked thereby because of their adherence to the wall of the passages in a preceding layer.

13. A device for removing microemboli from whole blood or the like comprising: a casing defined by a housing member and a base member secured together to define an interior chamber; an externally connectable flow inlet to the chamber in one member; an externally connectable flow outlet from the chamber in the other member; a plurality of layers of microemboli-removing material positioned in said chamber in obstructing relation to the flow path from the flow inlet to the flow outlet, said layers each consisting of foamed open cell polyurethane to define tortuous flow passages therethrough, said layers having progressively smaller effective pore sizes whereby the blood in flowing therethrough has the microemboli of a size to block passages in the layer prevented from flowing thereto by adherence to the walls of the passages in a preceding layer.

14. A device as defined in claim 13 including means defining a bypass passage around said layers of material for use in priming the device, and means movable to a locked position to close said bypass passage.

15. In a device for removing microemboli from whole blood or the like having a casing defining an interior chamber with a flow inlet and outlet; a plurality of layers of microemboli-removing material, each layer having a plurality of tortuous passageways therethrough; said layers being positioned in said chamber in obstructing relation to the flow path from said flow inlet to said flow outlet; the first of said layers closest to the flow inlet having an effective pore size greater than the size of all microemboli to be removed from the blood; the successive layers of said microemboli-removing material having progressively smaller effective pore size; said layers being formed of an open cell foamed plastic with effective pore sizes from about 150 microns to about 25 microns.

16. A device for removing microemboli from whole blood or the like according to claim 15 wherein said open cell foamed plastic forming said layers is a unitary structure of polyurethane.

* * * * *